(12) United States Patent
Shkolnikov et al.

(10) Patent No.: US 11,485,944 B2
(45) Date of Patent: Nov. 1, 2022

(54) MICROFLUIDIC CELLULAR MEMBRANE MODIFICATION DEVICES

(71) Applicant: HEWLETT-PACKARD DEVELOPMENT COMPANY, L.P., Spring, TX (US)

(72) Inventors: Viktor Shkolnikov, Palo Alto, CA (US); Daixi Xin, Palo Alto, CA (US)

(73) Assignee: Hewlett-Packard Development Company, L.P., Spring, TX (US)

(*) Notice: Subject to any disclaimer, the term of this patent is extended or adjusted under 35 U.S.C. 154(b) by 0 days.

(21) Appl. No.: 16/606,841

(22) PCT Filed: Apr. 4, 2018

(86) PCT No.: PCT/US2018/026028
§ 371 (c)(1),
(2) Date: Oct. 21, 2019

(87) PCT Pub. No.: WO2019/194799
PCT Pub. Date: Oct. 10, 2019

(65) Prior Publication Data
US 2021/0009931 A1    Jan. 14, 2021

(51) Int. Cl.
*C12M 3/06* (2006.01)
*C12M 1/00* (2006.01)
(Continued)

(52) U.S. Cl.
CPC .......... *C12M 23/16* (2013.01); *B01L 3/5027* (2013.01); *B01L 3/502715* (2013.01);
(Continued)

(58) Field of Classification Search
None
See application file for complete search history.

(56) References Cited

U.S. PATENT DOCUMENTS

| 2003/0087292 A1* | 5/2003 | Chen | C12Q 1/6834 |
| | | | 435/6.12 |
| 2005/0272159 A1* | 12/2005 | Ismagilov | C12Q 1/44 |
| | | | 436/34 |

(Continued)

FOREIGN PATENT DOCUMENTS

| CN | 101928666 B | 4/2013 |
| EP | 1804908 B1 | 7/2007 |

(Continued)

OTHER PUBLICATIONS

Valero, A. Single cell electroporation on chip. PhD thesis. University of Twente, Enschede, The Netherlands. Copyright 2006. Ana Valero. Publisher: Wohrmann Print Service, pp. 1-209. specif, pp. 16, 22, 26, 65.*

(Continued)

*Primary Examiner* — Brian R Gordon
(74) *Attorney, Agent, or Firm* — Thorpe North & Western LLP (57) ABSTRACT

The present disclosure is drawn to microfluidic cellular membrane modification devices. In one example, a microfluidic cellular membrane modification device can include a microfluidic channel including a pumping portion and an electric field portion. An electrode pair can be positioned about the electric field portion. A bidirectional pump can be in fluid communication with the microfluidic channel at the pumping portion to move fluid backward and forward through the electric field portion.

7 Claims, 8 Drawing Sheets

(51) Int. Cl.
  *C12M 1/42* (2006.01)
  *B01L 3/00* (2006.01)
  *F04B 19/00* (2006.01)
  *F04B 43/04* (2006.01)
  *F04B 43/06* (2006.01)
  *F04B 9/103* (2006.01)

(52) U.S. Cl.
  CPC ....... *B01L 3/502761* (2013.01); *C12M 29/00* (2013.01); *C12M 35/02* (2013.01); *F04B 9/1035* (2013.01); *F04B 19/006* (2013.01); *F04B 43/046* (2013.01); *F04B 43/06* (2013.01); *B01L 2300/0645* (2013.01); *B01L 2300/0883* (2013.01); *B01L 2400/0442* (2013.01)

(56) References Cited

U.S. PATENT DOCUMENTS

| | | | |
|---|---|---|---|
| 2009/0000948 A1 | 1/2009 | Wang et al. | |
| 2011/0213288 A1 | 9/2011 | Choi et al. | |
| 2013/0344539 A1* | 12/2013 | Ortac | C12P 19/34 435/91.2 |
| 2016/0274020 A1* | 9/2016 | Winkler | B01L 3/502707 |
| 2017/0283761 A1* | 10/2017 | Corso | C12M 27/00 |
| 2017/0355950 A1* | 12/2017 | Zohar | C12N 5/0657 |
| 2018/0021777 A1* | 1/2018 | Giri | G01N 15/0266 422/73 |
| 2018/0258379 A1* | 9/2018 | Zahn | C12N 13/00 |
| 2019/0100722 A1* | 4/2019 | Bernate | C12N 15/70 |
| 2019/0136224 A1* | 5/2019 | Garcia Dominguez | C12M 35/02 |
| 2019/0176111 A1* | 6/2019 | Markel | B41J 2/1433 |
| 2019/0300836 A1* | 10/2019 | Masquelier | C12M 35/04 |
| 2020/0071657 A1* | 3/2020 | Johnson | C12M 23/42 |
| 2020/0399579 A1* | 12/2020 | Bade | C12M 29/04 |
| 2022/0056392 A1* | 2/2022 | Corso | C12M 41/46 |

FOREIGN PATENT DOCUMENTS

| | | |
|---|---|---|
| WO | WO2007133710 A2 | 11/2007 |
| WO | WO2017040995 A1 | 3/2017 |
| WO | WO2017210334 A1 | 12/2017 |
| WO | WO2018058085 A1 | 3/2018 |

OTHER PUBLICATIONS

Woias, P. 2005. Micropumps—past, progress and future prospects. Sensors and Actuators 105: 28-38. specif. pp. 28, 30.*

Wang, Shengnian, et al. "Micro-/nanofluidics based cell electroporation" Biomicrofluidics 7, No. 1 (2013): 011301.

Zhan, Yihong, et al., "Electroporation of cells in microfluidic droplets." Analytical chemistry 81, No. 5 (2009), pp. 2027-2031.

* cited by examiner

MICROFLUIDIC CELLULAR MEMBRANE MODIFICATION DEVICES

BACKGROUND

Certain methods of modifying living cells involve introducing materials, such as DNA or protein, into the cells. Transfection refers to a process of introducing such materials through a cellular membrane into a cell. Cellular processes, organelles, and more can be studied by transfecting specific DNA molecules and proteins that incorporate into the cell's genome or utilize endogenous cellular machinery to function. This is one way in which genetically modified organisms with specific characteristics can be created and studied. Transfection can be carried out using several techniques, including viral, chemical, and electrotransfection, and there are various methodologies within these general transfection technique categories.

Reference will now be made to several examples that are illustrated herein, and specific language will be used herein to describe the same. It will nevertheless be understood that no limitation of the scope of the disclosure is thereby intended.

DETAILED DESCRIPTION

The present disclosure is drawn to microfluidic cellular membrane modification devices. In some examples, a microfluidic cellular membrane modification device can include a microfluidic channel with a pumping portion and an electric field portion. An electrode pair can be positioned about the electric field portion. A bidirectional pump can be in fluid communication with the microfluidic channel at the pumping portion to move fluid backward and forward through the electric field portion. In certain examples, the bidirectional pump can be integrated within the microfluidic channel. In other examples, the bidirectional pump can include a thermal resistor to move fluid via thermally-generated bubbles. In further examples, the device can include an ejection nozzle in fluid communication with the bidirectional pump to eject a portion of the fluid displaced by the thermally-generated bubbles. In other examples, the electric field portion of the microfluidic channel can include a constriction having a constricted cross-sectional area relative to a cross-sectional area of the pumping portion. In certain examples, the fluid to be loaded or loaded within the microfluidic channel can include cells, and the constricted cross-sectional area can be large enough to accommodate a single cell carried by the fluid. The microfluidic channel can have a serpentine shape crossing the electrode pair multiple times to provide multiple electric field portions. In other examples, the microfluidic channel can include a loop and the bidirectional pump can induce a net flow of fluid around the loop.

The present disclosure also extends to methods of modifying cells. In some examples, a method of modifying cells can include pumping a fluid including cells in a forward direction through a microfluidic channel. An electric field can be applied within the microfluidic channel as cells flow in the forward direction through the electric field and beyond within the microfluidic channel. The fluid can also be pumped in a backward direction through the microfluidic channel, and the cells can flow in the backward direction returning through the electric field. In further examples, pumping the fluid in the forward direction and backward direction can be repeated multiple times. A portion of the cells can flow through the electric field in both the forward and backward direction multiple times. In certain examples, the electric field can temporarily enlarge cell membrane pores, and the method can also include introducing a molecule into the cell through the cell membrane pores. In some examples, the electric field can be a non-pulsating electric field having a magnitude of 0.01 V/μm to 10 V/μm. In further examples, the cells can have a residence time during a single pass through the electric field of 0.01 ms to 10 s.

The present disclosure also includes microfluidic systems. In some examples, a microfluidic system can include a microfluidic device and a controller. The microfluidic device can include a microfluidic channel with a pumping portion and an electric field portion. An electrode pair can be positioned about the microfluidic channel to generate an electric field within the electric field portion and not within the pumping portion. A bidirectional pump can be in fluid communication with the microfluidic channel to pump fluid from the pumping portion alternately backward and forward multiple times through the electric field portion while the electric field is present. The controller can include a processor electrically coupled to the bidirectional pump and the electrode pair to control operation of the microfluidic device. In certain examples, the bidirectional pump can include a thermal resistor to move fluid via thermally-generated bubbles. The microfluidic device can also include an ejection nozzle in fluid communication with the bidirectional pump to eject a portion of the fluid displaced by the thermally-generated bubbles.

The microfluidic devices, systems, and methods described herein can be used for electrotransfection of DNA, proteins, other biological material or even other chemical materials such as drugs or other agents, into cells.

Electrotransfection devices can be challenging to operate with predictable results and without damaging the cells in some instances. For example, different varieties of cells can respond differently to electric fields, with differing pore sizes forming in the cellular membrane and differing maximum electric field strengths before cellular damage occurs. In many cases, a sufficiently strong electric field can cause pores in the cellular membrane to enlarge as long as the electric field is applied. If the electric field is removed after a certain amount of time, the pores may shrink and the cellular membrane may recover. However, if the electric field is applied for too long the pores may grow too large and permanently damage the cellular membrane so that the membrane will not recover. Furthermore, the pore size and length of time of opening the pores can affect the amount of DNA or other material that can be transfected through the pores. The optimal pore size or length of time of opening the pores can be different for differing materials to be transfected, as well as different cell types. Thus, specific combinations of cell types with material to be transfected can be associated with different optimal conditions, including electric field strength, time of application of the electric field, concentration of the material to be transfected, and other variables. Finding conditions that are effective for a particular type of cells and a particular material to be transfected can be very time consuming and labor intensive. Other methods of transfection can also have drawbacks. Viral transduction can carry a risk of introducing unwanted viral components into the cells and can be quite labor intensive. Lipofection can be labor intensive as well and can introduce unwanted surfactants into the cellular membrane.

The microfluidic cellular membrane modification devices described herein can make use of electrotransfection while also simplifying operation in order to achieve good transfection conditions for specific cell types and materials to be transfected. In some cases, the microfluidic devices can include bidirectional pumps that can be precisely controlled to move small volumes of fluid through the microfluidic channel. This can allow for fine adjustment of the flow rate of fluid through the electric field, and consequently the amount of time each cell spends in the electric field. Because the pumps are bidirectional, cells can be moved repeatedly through the electric field in a forward direction and a backward direction. The residence time of the cells within the electric field can be modified to increase the amount of material transfected into the cells while the cellular membrane pores are enlarged. The cells can also have a repeated rest time outside of the electric field. The rest time can be modified to allow the pores to relax before re-entering the electric field. In some examples, the microfluidic channel can include a portion that is sufficiently wide for a single cell to pass through, i.e., cells pass through single file. In some cases, this portion of the microfluidic channel can be a constriction located within the electric field. Passing cells single file through the electric field in this way can increase the uniformity of transfection for the cells. For example, each cell can have approximately the same residence time in the electric field, so that each cell receives approximately the same amount of transfected material. Thus, the devices described herein can allow for fine control over the residence time of cells in the electric field, rest time of the cells outside the electric field, concentration of material to be transfected in the fluid surrounding the cells, and the strength of the electric field. These parameters can be adjusted for transfecting any combination of cell type and material to be transfected. The amount of material transfected into the cells can also be controlled by adjusting the number of times the cells pass through the electric field.

Figure 1A:
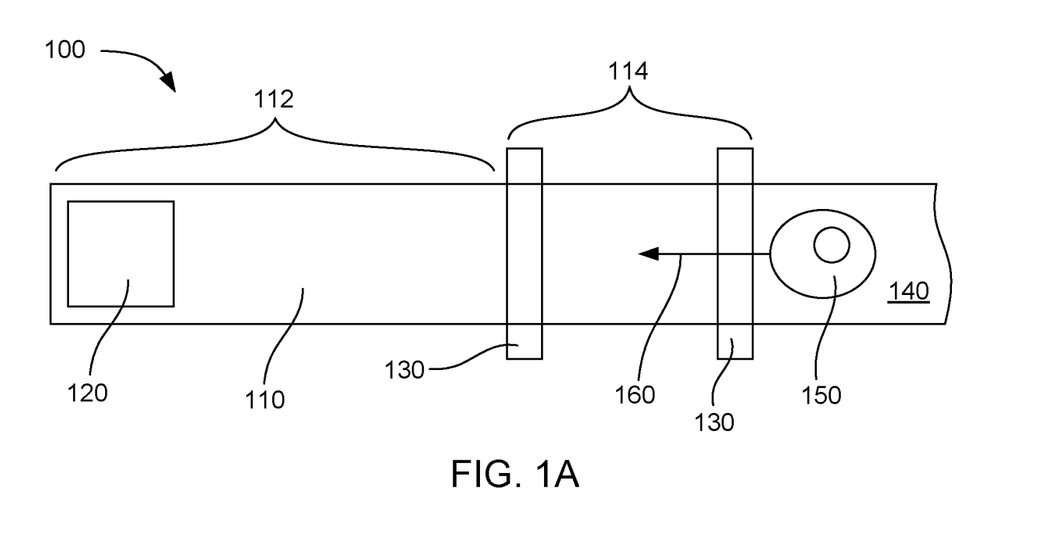
FIGS. 1A-1C are schematic views of an example microfluidic cellular membrane modification device in accordance with an example of the present technology.

With this description in mind, one example of a microfluidic cellular membrane modification device is shown in FIG. 1A. This microfluidic cellular membrane modification device 100 includes a microfluidic channel 110, a bidirectional pump 120, and a pair of electrodes 130. The microfluidic channel includes a pumping portion 112 and an electric field portion 114. The microfluidic channel can be loaded with a fluid 140 that includes a cell 150.

Figure 1B:
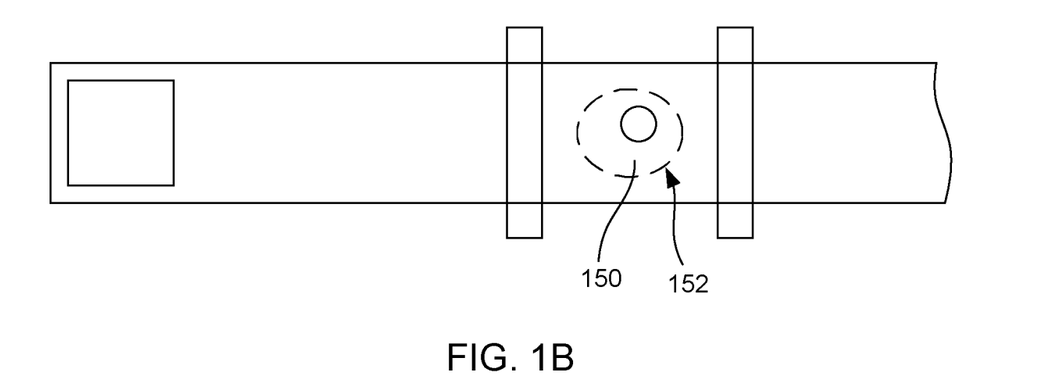
Figure 1C:
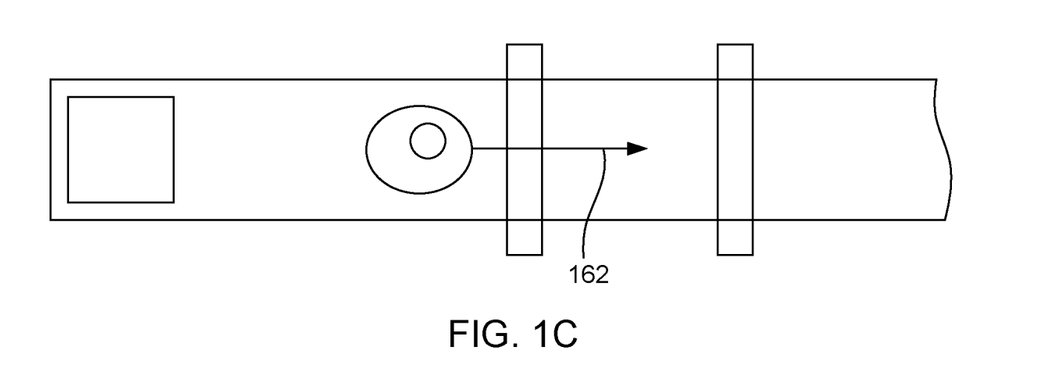

FIGS. 1A-1C also illustrate the motion of the cell 150 as the bidirectional pump 120 pumps the fluid 140 in the forward direction 160. The cell begins in FIG. 1A outside the electric field generated by the electrode pair 130. FIG. 1B shows the cell after the cell has moved into the electric field between the electrodes. The electric field enlarges pores 152 in the cellular membrane, allowing DNA or other molecules in the fluid to enter the cell. FIG. 1C shows the cell after the cell has moved out the other side of the electric field. While the cell is outside the electric field, the pores close. The bidirectional pump can then pump the fluid in the backward direction 162, and the cell will travel backward through the electric field. This cycle can be repeated to increase the amount of material introduced into the cell.

Figure 2A:
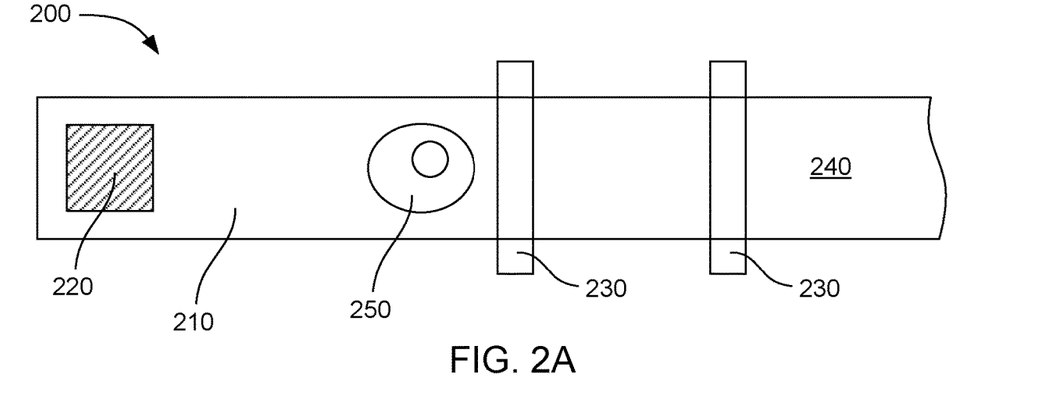
FIGS. 2A-2C are schematic views of another example microfluidic cellular membrane modification device in accordance with an example of the present technology.
Figure 2B:
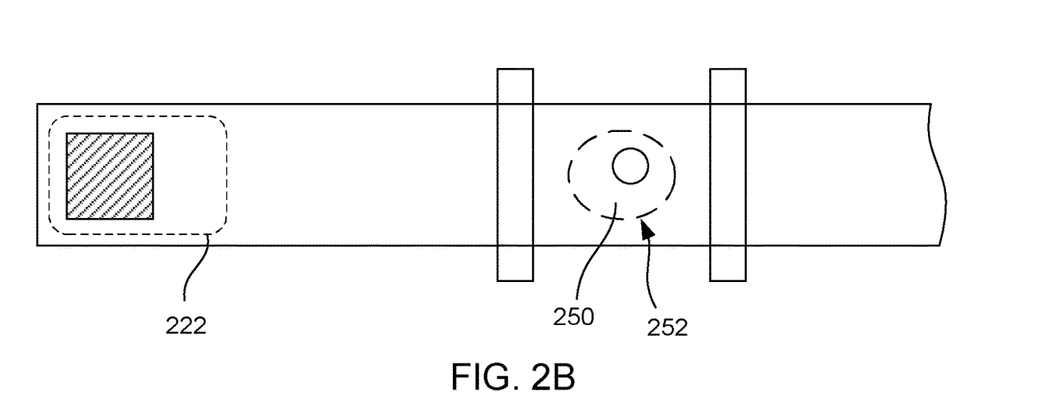
Figure 2C:
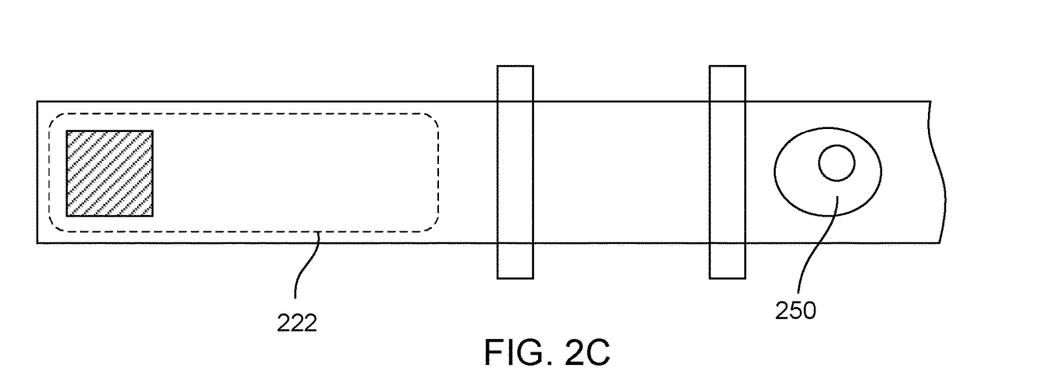

FIGS. 2A-2C illustrate another example microfluidic cellular membrane modification device 200. In this example, a thermal resistor 220 acts as the bidirectional pump. Applying an electric current to the thermal resistor can generate heat. When enough energy is applied, a vapor bubble 222 can nucleate in the fluid 240 within the microfluidic channel 210. The vapor bubble can displace fluid, causing the fluid to flow through the microfluidic channel. FIG. 2A shows a cell 250 in the microfluidic channel outside of the electric field generated by electrodes 230. As the vapor bubble grows, the fluid flows away from the growing bubble. FIG. 2B shows the cell after it has been carried by the flow of fluid into the electric field between the electrodes. The electrode field causes pores 252 in the cellular membrane to be enlarged. As the vapor bubble continues to grow, the cell moves across the electric field and out of the electric field, as shown in FIG. 2C. At this point, the vapor bubble can collapse, and fluid can fill in the volume occupied by the vapor bubble. This flow can cause the cell to move through the electric field once again. This process can be repeated multiple times by forming additional vapor bubbles using the thermal resistor.

In some examples, the thermal resistor used in the microfluidic devices can be formed by depositing a thin film of conductive material on a surface of the microfluidic channel. In various examples, the conductive material can include a metal, a metal alloy, silicon, carbon, or combinations thereof. Metals that can be used in the thermal resistor can include gold, titanium, vanadium, chromium, cobalt, nickel, zirconium, niobium, molybdenum, rhodium, palladium, hafnium, tantalum, tungsten, iridium, platinum, or alloys thereof. The thermal resistor can be connected to a power source through electrically conductive traces, vias, wires, and so on. In some examples, the thermal resistor can be similar in composition and design to a thermal resistor used in a thermal inkjet printhead of a thermal inkjet printer.

In other examples, the bidirectional pump can include a piezoelectric element. In these examples, the pumping action can be similar to the examples that employ a thermal resistor, but the piezoelectric element can displace fluid instead of the thermal resistor forming a vapor bubble to displace fluid. Applying an electric current to the piezoelectric element can cause the piezoelectric element to change volume and/or shape. The piezoelectric element can be placed in or near the pumping portion of the microfluidic channel such that the change in volume or shape will displace fluid in the pumping portion of the channel. This displacement can cause fluid to flow in the backwards direction through the microfluidic channel. When the electric current is removed from the piezoelectric element, the piezoelectric element can return to its original shape and the displaced fluid can return to fill in the volume left behind by the piezoelectric element. As explained above, the backward and forward motion of the fluid can carry cells in the fluid through the electric field. In some examples, the piezoelectric element can be similar to a piezoelectric element used in a piezoelectric inkjet printhead of a piezoelectric inkjet printer.

In still other examples, other types of bidirectional pumps may be used. In some examples, the bidirectional pump can be integrated with the microfluidic channel, such as being located within the microfluidic channel. In alternative examples, the bidirectional pump can be a separate component that is connected to the microfluidic channel. Other types of pumps that may be used can include peristaltic pumps, electroosmotic pumps, membrane displacement pumps, gear pumps, vane pumps, and others.

In some examples, the bidirectional pump can include a thermal resistor that generates bubbles to displace a volume of fluid in the microfluidic channel. A bubble generated by the thermal resistor may displace a volume of fluid from 1 pL to 1 µL. In some examples, the volume of fluid displaced by the bubble can be sufficient to cause cells in the fluid to travel from one side of the electric field through the electric field to the other side. In further examples, the thermal resistor can generate bubbles with a frequency of up to 10 kHz. Accordingly, in some examples the cells can travel through the electric field the same number of passes per second. In certain examples, a cell in the fluid can have a residence time in the electric field of 0.01 ms s to 10 s each time the cell passes through the electric field.

In further examples, the microfluidic device can also include an ejection nozzle in fluid communication with the bidirectional pump. The ejection nozzle can eject a portion of the fluid displaced by the bidirectional pump. For example, if the bidirectional pump includes a thermal resistor to generate vapor bubbles, then a portion of the fluid displaced by each vapor bubble can be ejected out of the ejection nozzle. In some examples, this can operate similar to an inkjet printhead in an inkjet printer, in which fluid ink is ejected out of a nozzle by the vapor bubbles generated by the thermal resistor. In the case of the microfluidic devices described herein, a portion of cells in the fluid can also be ejected along with the fluid. In some examples, the ejection nozzle can eject the fluid and cells out of the microfluidic device. In certain examples, the fluid and cells can be collected in another vessel, such as a well plate or other container. In other examples, the ejection nozzle can direct fluid and cells into a different microfluidic channel or into an additional chamber within the microfluidic device. For example, the ejection nozzle may direct fluid and cells into a holding chamber within the microfluidic device where the fluid and cells can be stored and collected at a later time. In some examples, the ejection nozzle can eject a volume of fluid from 1 pL to 1 uL each time the ejection nozzle fires.

Figure 3:
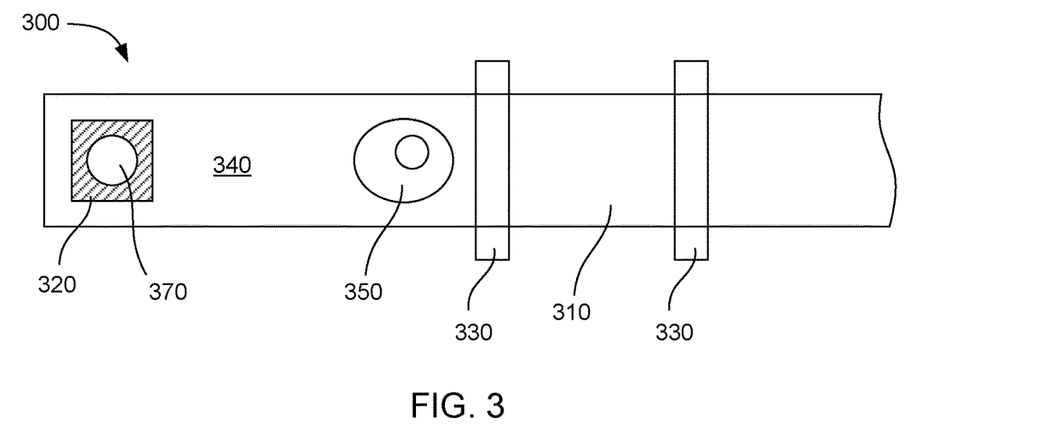
FIG. 3 is a schematic view of yet another example microfluidic cellular membrane modification device in accordance with an example of the present technology.

FIG. 3 shows another example microfluidic cellular membrane modification device 300 including an ejection nozzle 370. A thermal resistor 320 can be located at or near the nozzle so that vapor bubbles generated by the thermal resistor push some fluid 340 out of the nozzle. As explained above, some displaced fluid also moves through the microfluidic channel 310. The fluid can carry cells 350 into the electric field between the electrodes 330.

In some examples, the bidirectional pump can induce a net flow in one direction through the microfluidic channel. More specifically, the bidirectional pump can pump fluid in both the forward and backward direction so that cells in the fluid pass through the electric field, but in some examples the bidirectional pump can pump the fluid at a higher flow rate in one direction so that the overall flow of the fluid over multiple backward and forward cycles is in one direction. In one example, the microfluidic device can include an ejection nozzle as explained above and the bidirectional pump can induce a net flow of fluid in the direction toward the ejection nozzle. In the example shown in FIG. 3, the thermal resistor 320 may generate vapor bubbles that displace a portion of fluid 340 in a backward direction toward the electrodes 330 while a portion of fluid is ejected out of ejection nozzle 370. When the vapor bubbles collapse, fluid from the microfluidic channel can flow in to occupy the volume left behind by the vapor bubble. The volume of fluid flowing in to replace the vapor bubble can be greater than the volume of fluid that was displaced toward the electrodes when the vapor bubble was formed. Thus, the overall net flow of fluid can be in the direction from the electrodes toward the ejection nozzle. In some examples, the net flow rate can be selected so that cells in the fluid can pass through the electric field a desired number of times before the cells finally flow to the ejection nozzle. In further examples, the cells can be ejected from the microfluidic device when the cells reach the ejection nozzle.

In certain examples, the microfluidic channel can include a loop and the bidirectional pump can induce a net flow of fluid around the loop. Cells in the fluid in the microfluidic channel can pass through the electric field multiple times as the bidirectional pump cycles from the forward direction to the backward direction, and the number of times the cells pass through the electric field can be multiplied by the number of times the cells travel around the loop. Thus, the overall number of passes through the electric field can be increased in this example.

Figure 4:
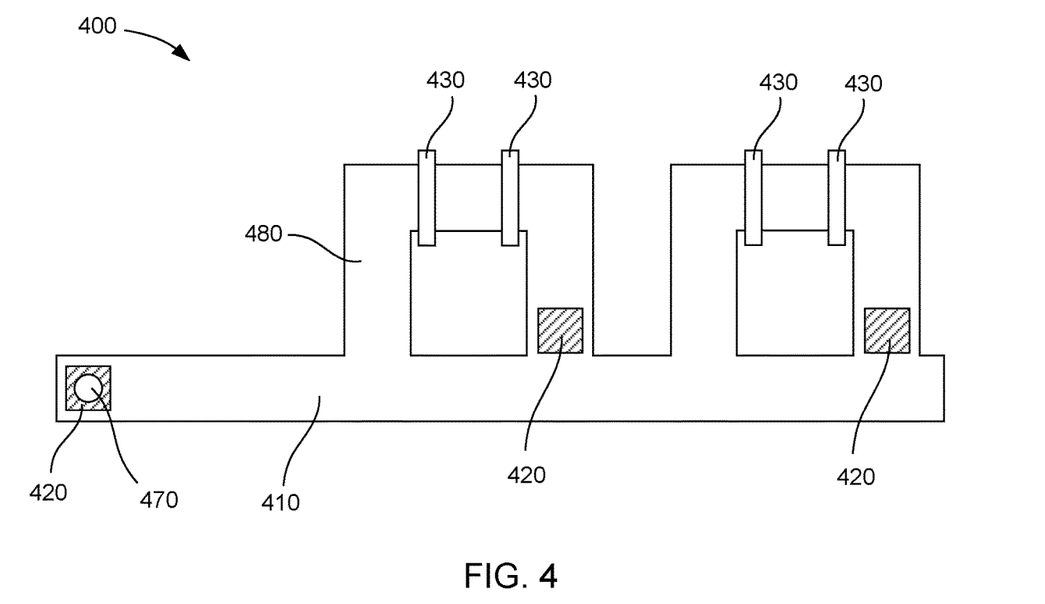
FIG. 4 is a schematic view of yet another example microfluidic cellular membrane modification device in accordance with an example of the present technology.

FIG. 4 shows an example microfluidic cellular membrane modification device 400 including multiple loops 480 in the microfluidic channel 410. Each loop can include a thermal resistor 420 to act as a bidirectional pump. These thermal resistors can generate a net flow of fluid around the loops. Cells in the fluid can travel back and forth through the electric fields between electrodes 430 each time the thermal resistors generate a vapor bubble in the loops. The cells can also flow around the loop multiple times to increase the number of times the cells pass through the electric fields. The device also includes another thermal resistor with an ejection nozzle 470 in the microfluidic channel to eject fluid and electrotransfected cells out of the device.

In some examples, the microfluidic devices described herein can be fabricated using photolithography. The microfluidic channel can be formed from multiple layers, and the shape of the microfluidic channel can be formed by developing a photoresist material. In certain examples, the layers can be formed from an epoxy-based photoresist. In one example, the layers can be formed from SU-8 or SU-8 2000 photoresist, which are epoxy-based negative photoresists. Specifically, SU-8 and SU-8 200 are Bisphenol A Novolac epoxy-based photoresists that are available from various sources, including MicroChem Corp. These materials can be exposed to UV light to become crosslinked, while portions that are unexposed remain soluble in a solvent and can be washed away to leave voids.

In certain examples, a microfluidic device can be fabricated by applying a primer layer to a substrate. In one example, a thermal resistor and a pair of electrodes can then be deposited in their respective locations over the primer layer. In other examples, the thermal resistor and/or electrodes can be formed directly on the substrate and the primer can then be applied over the thermal resistor and/or electrodes. The primer layer may then be removed from the tops of the thermal resistor and/or electrodes. A microfluidic layer can then be deposited over the primer layer. The microfluidic layer can include the microfluidic channel walls that define the microfluidic channel. A top layer or ceiling can then be applied over the microfluidic layer.

In some examples, the substrate can be formed of a silicon material. For example, the substrate can be formed of single crystalline silicon, polycrystalline silicon, gallium arsenide, glass, silica, ceramics or a semiconducting material. In a particular example, the substrate can have a thickness from about 50 μm to about 1200 μm.

In further examples, the primer layer can be a layer of a photoresist material, such as SU-8, with a thickness from about 2 μm to about 100 μm.

The microfluidic layer can be formed by exposing a layer of photoresist with a pattern of walls to define the microfluidic channel, and then washing away the unexposed photoresist. This layer can be formed by spin coating a liquid photoresist on the primer layer and then developing the layer, by laminating a dry photoresist film, or by a combination of both techniques. In some examples, the microfluidic layer can have a thickness from about 2 μm to 100 μm. Thus, the microfluidic channel can have a wall height corresponding to the height of the microfluidic layer. The microfluidic channel can be formed having a width from about 2 μm to about 100 μm, from about 10 μm to about 50 μm, or from about 20 μm to about 30 μm.

In certain examples, the top layer or ceiling can be formed by laminating a dry film photoresist over the microfluidic layer and exposing the dry film photoresist with a UV pattern to form the ceiling of the microfluidic channel. In some examples, the top layer can have a thickness from about 2 μm to about 200 μm.

In certain examples, a pair of electrodes can be positioned about the microfluidic channel to generate an electric field within the channel. In some examples, the electrodes can be formed by depositing a layer of a conductive material at or near the floor of the microfluidic channel. Although the electrodes are not located on opposite sides of the channel in this example, the electrodes can still generate a sufficient electric field within the channel. In other examples, the electrodes can be located across the channel one from another. For example, one electrode can be on the floor of the channel and the other electrode can be on the ceiling of the channel so that an electric field is generated within the channel between the two electrodes. In another example, the electrodes can be on opposite walls of the channel.

The electrodes may be made of any conductive material that can direct an electrical field within the microfluidic channel as described herein. In some cases, the electrodes can be a layer of any of the conductive materials described above in connection with the thermal resistors that can be used in some examples. In certain examples, the electrodes can have a voltage supplied to them via a number of electrical traces formed within and/or on the microfluidic device.

In further examples, the electrodes can have an applied voltage from 5 V to 70 V. The optimal voltage may vary considerably depending on the spacing of the electrodes, the type of cells being used, the residence time of the cells in the electric field, and the type of material being introduced into the cells. In certain examples, the electrodes can be spaced apart at a distance from 250 μm to 300 μm. In further examples, the electric field generated by the electrodes can have an electric field strength from 0.01 V/μm to 10 V/μm. In still further examples, the voltage applied to the electrodes may be an alternating current (AC) or direct current (DC) voltage. In some examples, an alternating current having a voltage from 30V to 50V and a frequency from 50 kHz to 500 kHz can be used.

In order to increase the uniformity of the exposure of cells to the electric field, some examples can include a constriction of the microfluidic channel in the electric field. The constriction can have a cross-sectional area that is smaller than a cross-sectional area of the pumping portion of the microfluidic channel. In certain examples, the constricted cross-sectional area can be large enough to accommodate a single cell carried by the fluid so that the cells pass through the constriction in a single-file manner.

Figure 5:
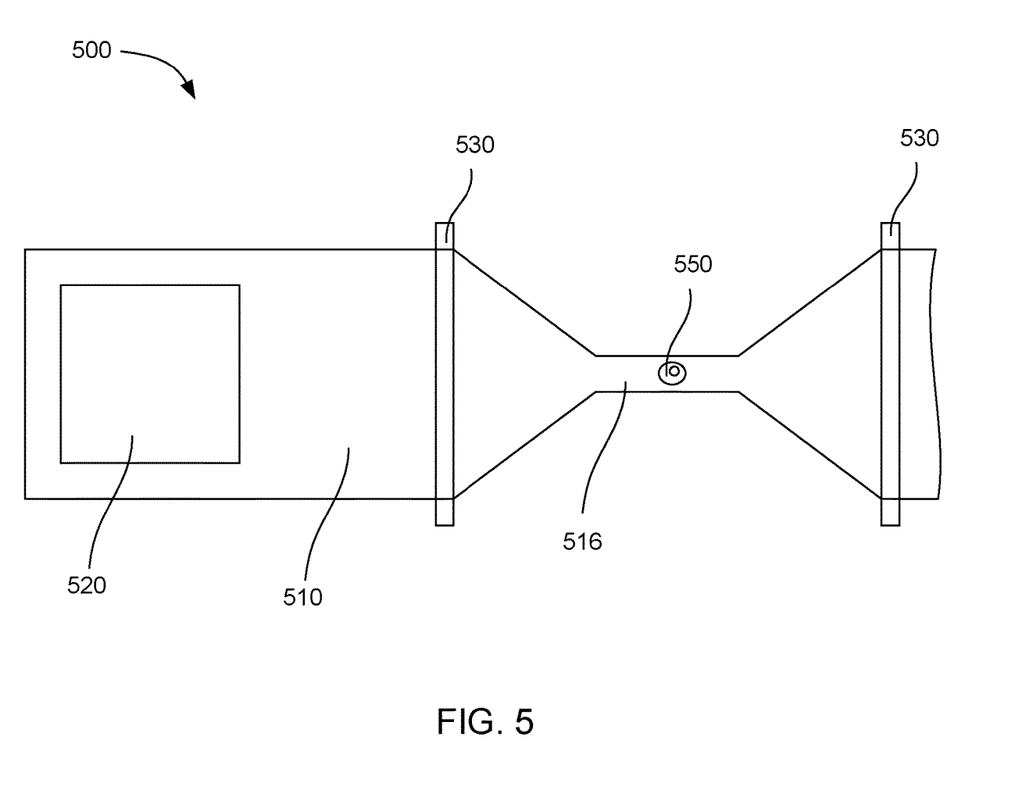
FIG. 5 is a schematic view of another example microfluidic cellular membrane modification device in accordance with an example of the present technology.

FIG. 5 illustrates an example microfluidic cellular membrane modification device 500 that includes a constriction 516 in the microfluidic channel 510 between the pair of electrodes 530. The device also includes a bidirectional pump 520 that can pump fluid in the microfluidic channel backward and forward so that a cell 550 travels through the constriction between the electrodes multiple times.

The dimensions of the constriction of the microfluidic channel may be varied based on the type of cell to be electroporated by the electrodes. In some examples, the length of the constriction can be from 50 to 130 μm. In other examples, the length of the constriction can be from 60 to 120 μm. In further examples, the width of the constriction can be from 5 to 35 μm. In still further examples, the width of the constriction can be from 15 to 30 μm. In other examples, a maximum width of the microfluidic channel, i.e., in the non-constricted portions, can be from 100 to 200 μm. In further examples, the maximum width of the microfluidic channel can be from 140 to 160 μm. In other examples, the distance between an end of the constricted portion of the microfluidic channel and the nearest electrode can be from 80 to 100 μm. In a particular example, the distance between the end of the constricted portion of the microfluidic channel and the nearest electrode can be about 90 μm. In one example, the width of the electrodes can be 15 μm.

In examples that include a constricted portion of the microfluidic channel, the electrodes can be located on either end of the constricted portion. In some examples, the electrodes can be located in the non-constricted portion of the microfluidic channel. In particular examples, the electrodes can be located at the transition where the channel width begins to constrict from the non-constricted width toward the constricted width. In certain examples, the electrodes can be spaced apart from 250 μm to 450 μm. In further examples, the electrodes can be spaced apart from 300 μm to 400 μm. In one particular example, the electrodes can be spaced apart about 350 μm.

In some examples, a microfluidic cellular membrane modification device can be empty, containing no fluid. This may be the state of the device before it is used, i.e., before the device is filled with fluid containing cells to be electrotransfected. In other examples, the device can contain the fluid inside the microfluidic channel. In various examples, the fluid can include cells to be transfected, a buffer, and a material to be introduced into the cells. The cells can be any type of cells that are desired to be modified using the device. In certain examples, the cells can be unicellular organisms such as bacteria. In alternative examples, the cells can be from a larger organism such as animal cells or human cells.

In certain examples, the cells can be from an immortal cell line such as HeLa cells. In some examples, the fluid used in the microfluidic device may have a cell concentration from $10^4$ to $10^6$ cells/mL.

The fluid used in the microfluidic cellular membrane modification devices described herein can also include a buffer. The buffer can generally be formulated to ensure cell viability. In some cases, a buffer specially designed for electroporation or electrotransfection can be used. Non-inclusive examples of buffers can include BTXPRESS™ Electroporation Solution from BTX, Opti-MEM™ media from Gibco, and other cell buffers.

The material to be transfected can include a variety of molecules or particles to be introduced into the cells. In some examples, the material to be transfected can be a DNA plasmid. In further examples, multiple DNA plasmids can be introduced together. Additional examples of materials that may be transfected can include proteins, antibodies, RNA, and others. In certain examples, the concentration of the material to be transfected can be from 10 μg to 100 μg.

Figure 6:
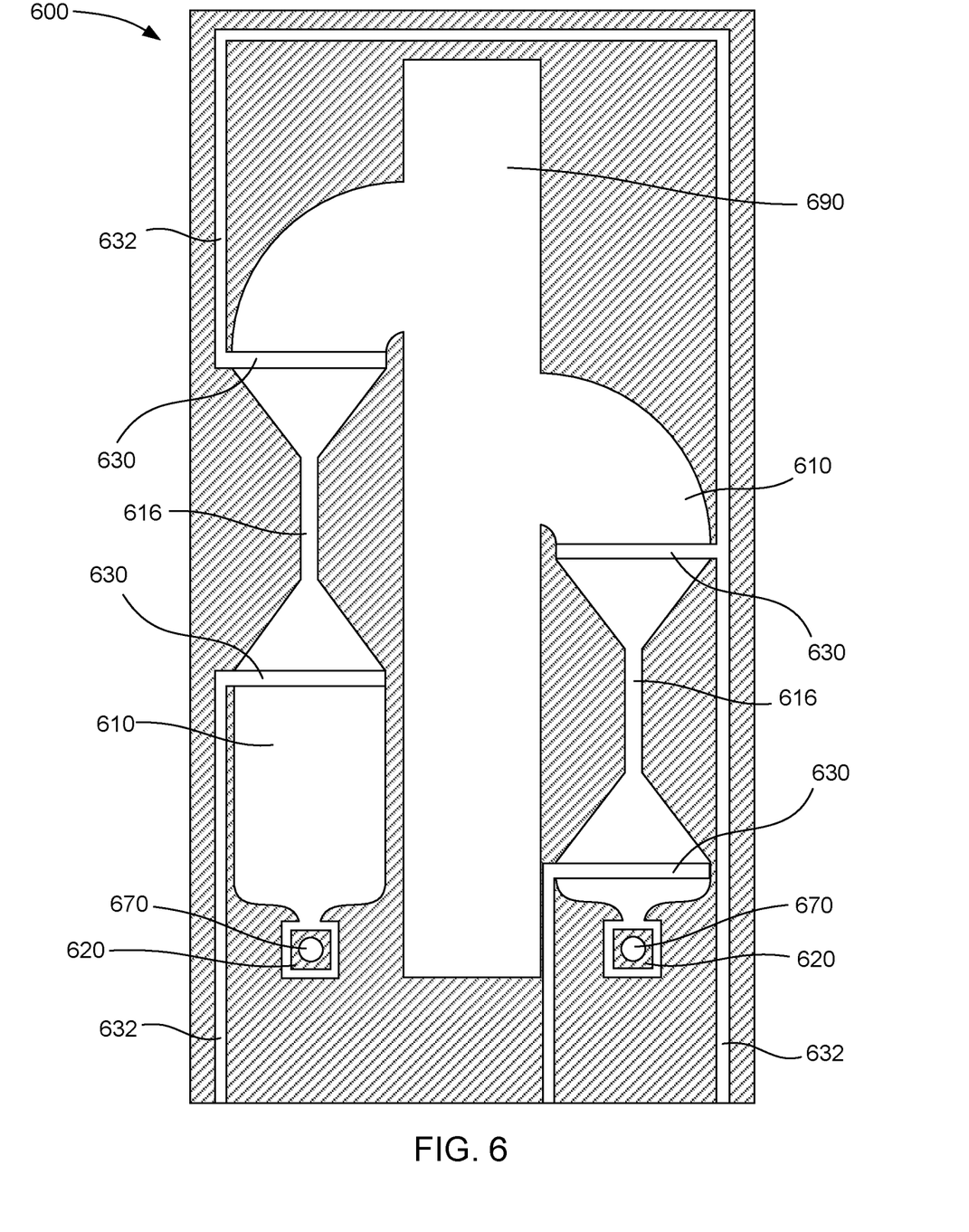
FIG. 6 is a cross-sectional schematic view of yet another example microfluidic cellular membrane modification device in accordance with an example of the present technology.

In further examples, microfluidic cellular membrane modification devices can be designed to have multiple microfluidic channels and multiple bidirectional pumps. FIG. 6 shows a cross-sectional view of one example microfluidic cellular membrane modification device 600 that includes two microfluidic channels 610. Thermal resistors 620 pump fluid in the microfluidic channels backward and forward through constrictions 616. The thermal resistors also eject fluid from the ejection nozzles 670. Electrode pairs 630 are located around the constrictions. A voltage can be applied to the electrodes through conductive traces 632. As fluid flows through the microfluidic channels and is ejected out the ejection nozzles, additional fluid can flow into the microfluidic channels from reservoir 690.

Figure 7:
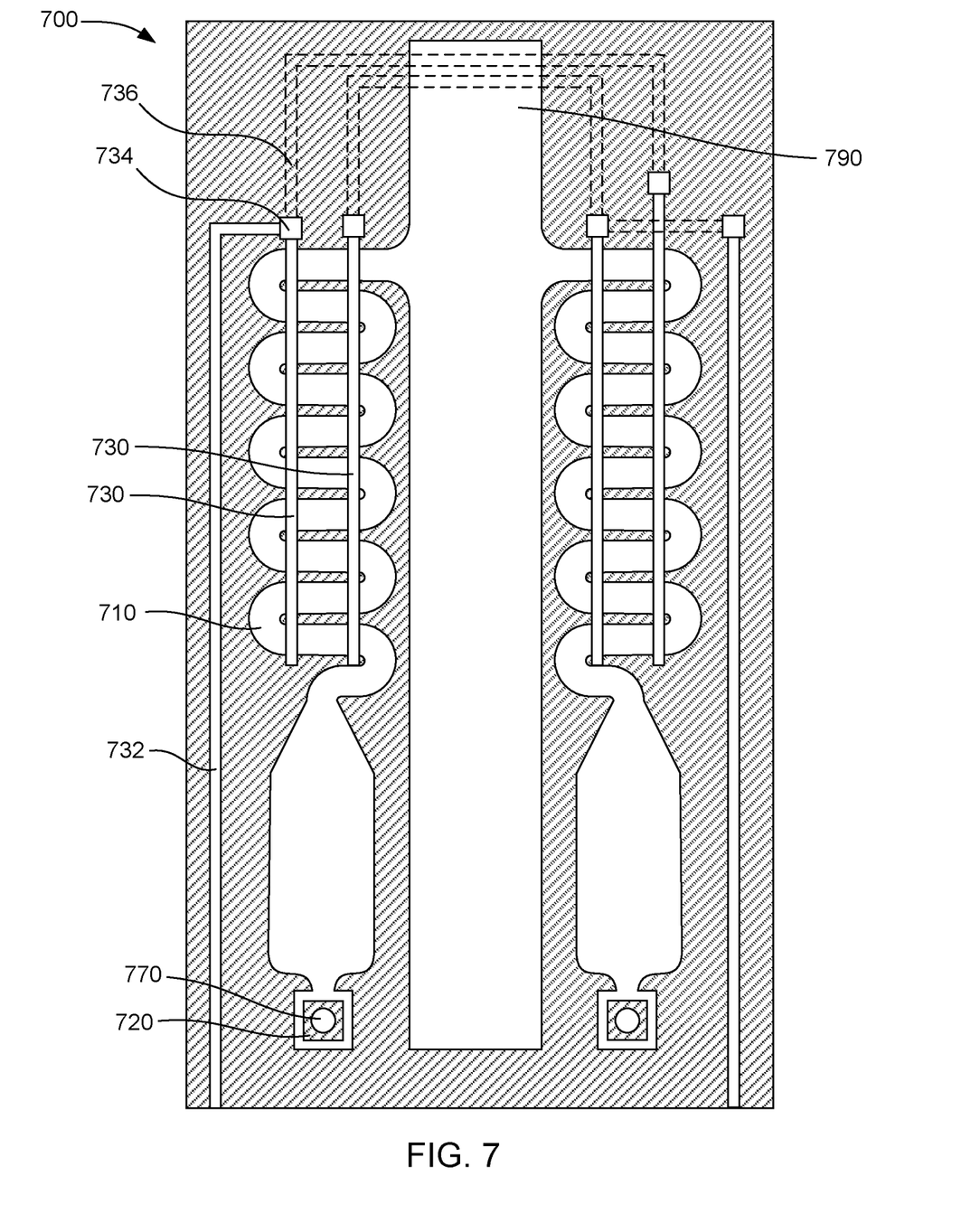
FIG. 7 is a cross-sectional schematic view of yet another example microfluidic cellular membrane modification device in accordance with an example of the present technology.

In other examples, the microfluidic channel can have a serpentine shape that crosses the electric field multiple times. The microfluidic channel can have multiple electric field portions where cells in the microfluidic channel are exposed to the electric field. FIG. 7 shows one example microfluidic cellular membrane modification device 700 that includes serpentine shaped microfluidic channels 710. The serpentine channels direct fluid containing the cells to be electrotransfected through the electric field between electrodes 730 multiple times. The net flow of the fluid is in the direction from the reservoir 790 to the thermal resistor 720 and ejection nozzle 770. A voltage can be applied to the electrodes through conductive traces 732. In this example, the traces connect to the electrodes through conductive vias 734 and additional conductive traces 736 on the opposite side of the device.

Figure 8:
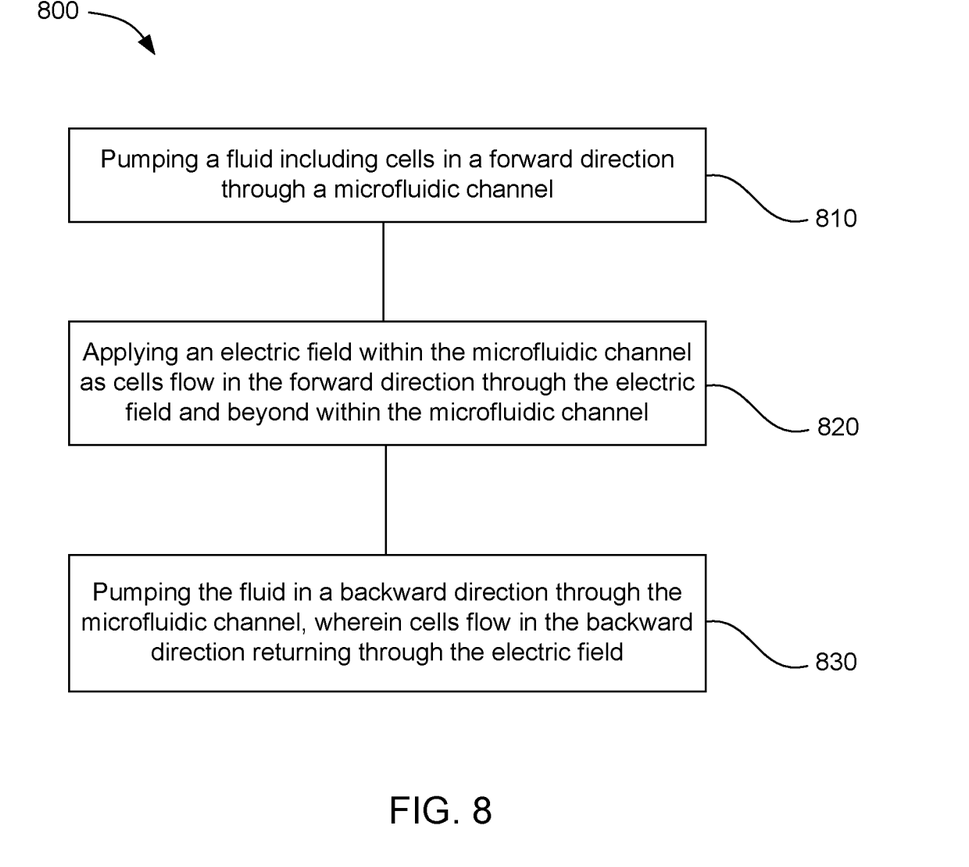
FIG. 8 is a flowchart of an example method of modifying cells in accordance with an example of the present technology.

The present disclosure also extends to methods of modifying cells. FIG. 8 is a flowchart illustrating one example method 800 of modifying cells. The method includes pumping 810 a fluid including cells in a forward direction through a microfluidic channel; applying 820 an electric field within the microfluidic channel as cells flow in the forward direction through the electric field and beyond within the microfluidic channel; and pumping 830 the fluid in a backward direction through the microfluidic channel, wherein cells flow in the backward direction returning through the electric field.

In further examples, methods of modifying cells can be performed using any of the devices and techniques described above. In some examples, the fluid can be pumped in the forward direction and the backward direction multiple times. A portion of the cells can flow through the electric field in both the forward and backward direction multiple times. The method can also include introducing a molecule into the cells through cell membrane pores that are enlarged by the electric field. In certain examples, the electric field can be a constant electric field, i.e., the electric field can be non-pulsated. In one example, the electric field can be a non-pulsating electric field with a magnitude of 0.01 V/μm to 1 V/μm. In further examples, the fluid can be pumped forward and backward at a flow rate such that the cells in the fluid have a residence time during a single pass through the electric field from 0.01 ms to 10 s.

Figure 9:
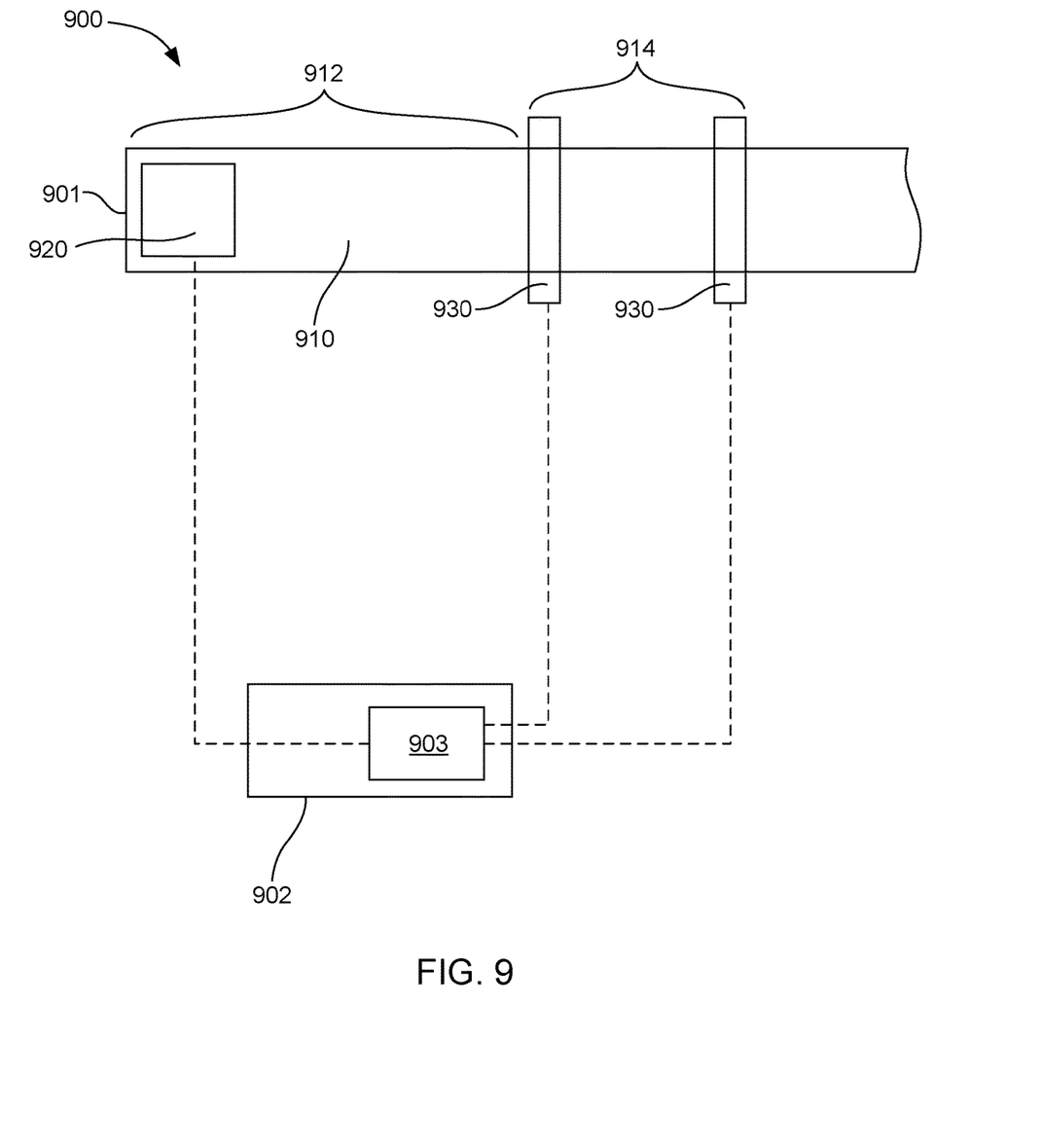
FIG. 9 is a schematic view of an example microfluidic system in accordance with an example of the present technology.

The present disclosure also extends to microfluidic systems that can include the microfluidic cellular membrane modification devices described above. FIG. 9 shows one example of a microfluidic system 900. The system includes a microfluidic device 901 and a controller 902. The microfluidic device includes a microfluidic channel 910 that includes a pumping portion 912 and an electric field portion 914. A pair of electrodes 930 is positioned about the microfluidic channel to generate an electric field within the electric field portion and not within the pumping portion. A bidirectional pump 920 is in fluid communication with the microfluidic channel. The bidirectional pump can pump fluid from the pumping portion alternately backward and forward multiple times through the electric field portion while the electric field is present. The controller can include a processor 903 electrically coupled to the bidirectional pump and the electrode pair to control operation of the microfluidic device.

In various examples, microfluidic systems can include any of the features of the microfluidic devices described above. In certain examples, the controller can be integrated into the microfluidic device as a single device. In other examples, the microfluidic device can be a separate component that is attachable to the controller. In certain examples, the microfluidic device can be a disposable cartridge that can be attached to the controller such that the controller can control the electrodes and bidirectional pumps of the microfluidic device.

It is noted that, as used in this specification and the appended claims, the singular forms "a," "an," and "the" include plural referents unless the content clearly dictates otherwise.

As used herein, the term "about" is used to provide flexibility to a numerical range endpoint by providing that a given value may be "a little above" or "a little below" the endpoint. The degree of flexibility of this term can be dictated by the particular variable and can be determined based on experience and the associated description herein.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, dimensions, amounts, and other numerical data may be presented herein in a range format. It is to be understood that such range format is used merely for convenience and brevity and should be interpreted flexibly to include the numerical values explicitly recited as the limits of the range, and also to include all the individual numerical values or sub-ranges encompassed within that range as if each numerical value and sub-range is explicitly recited. For example, a weight ratio range of about 1 wt % to about 20 wt % should be interpreted to include the explicitly recited limits of 1 wt % and about 20 wt %, and also to include individual weights such as 2 wt %, 11 wt %, 14 wt %, and sub-ranges such as 10 wt % to 20 wt %, 5 wt % to 15 wt %, etc.

As a further note, in the present disclosure, it is noted that when discussing the microfluidic devices, methods, and systems described herein, each of these discussions can be considered applicable to each of these examples, whether or not they are explicitly discussed in the context of that example. Thus, for example, in discussing details about the microfluidic cellular membrane modification devices, such discussion also refers to the methods and systems, and vice versa.

While the disclosure has been described with reference to certain examples, various modifications, changes, omissions, and substitutions can be made without departing from the spirit of the disclosure. It is intended, therefore, that the disclosure be limited by the scope of the following claims.

What is claimed is:

1. A microfluidic cellular membrane modification device, comprising:
    a microfluidic channel;
    an electrode pair positioned to generate an electric field within an electric field portion of the microfluidic channel; and
    a bidirectional pump integrated within a pumping portion of the microfluidic channel to move fluid backward and forward through the electric field portion, wherein the pumping portion is a different portion of the microfluidic channel from the electric field portion;
    wherein the microfluidic channel is positioned over the electrode pair and the microfluidic channel has a serpentine shape crossing the electrode pair multiple times to provide multiple electric field portions.

2. The microfluidic device of claim 1, wherein the bidirectional pump comprises a thermal resistor to move fluid via thermally-generated bubbles.

3. The microfluidic device of claim 2, further comprising an ejection nozzle connected to the bidirectional pump by the microfluidic channel to eject a portion of the fluid displaced by the thermally-generated bubbles.

4. The microfluidic device of claim 1, wherein the electric field portions include a constriction having a constricted cross-sectional area relative to a cross-sectional area of the pumping portion, wherein the cross-sectional areas are taken perpendicular to a direction of fluid flow through the microfluidic channel.

5. The microfluidic device of claim 4, wherein the microfluidic device includes the fluid loaded within the microfluidic channel, wherein the fluid includes cells, and wherein the constricted cross-sectional area is large enough to accommodate a single cell carried by the fluid.

6. The microfluidic device of claim 1, wherein the microfluidic channel comprises a loop wherein the bidirectional pump induces a net flow of fluid around the loop.

7. The microfluidic device of claim 4, wherein the constriction has a width from 5 µm to 35 µm and the pumping portion has a width from 100 µm to 200 µm.

* * * * *